US006508982B1

(12) United States Patent
Shoji

(10) Patent No.: US 6,508,982 B1
(45) Date of Patent: Jan. 21, 2003

(54) AIR-CLEANING APPARATUS AND AIR-CLEANING METHOD

(75) Inventor: Masami Shoji, Sendai (JP)

(73) Assignee: Kabushiki Kaisha Seisui, Sendai (JP)

( * ) Notice: Subject to any disclaimer, the term of this patent is extended or adjusted under 35 U.S.C. 154(b) by 0 days.

(21) Appl. No.: 09/217,200

(22) Filed: Dec. 22, 1998

(30) Foreign Application Priority Data

Apr. 27, 1998  (JP) ............................................. 10-116321

(51) Int. Cl.[7] .......................... A61L 2/00; B01J 19/08; H05F 3/00; B03C 3/00; B03C 3/41
(52) U.S. Cl. ............................ 422/22; 422/5; 422/121; 422/186.04; 422/186.07; 204/164; 204/176; 96/60; 96/65; 96/69; 96/97
(58) Field of Search ................................ 422/121, 120, 422/122, 4, 22, 186.3, 186.04, 186.07; 204/164, 176; 96/65, 97, 69, 60

(56) References Cited

U.S. PATENT DOCUMENTS

| | | | | |
|---|---|---|---|---|
| 3,711,743 A | * | 1/1973 | Bolasny .......................... 317/3 |
| 4,227,894 A | * | 10/1980 | Proynoff ....................... 55/126 |
| 4,496,375 A | * | 1/1985 | Le Vantine ................... 55/131 |
| 4,643,745 A | * | 2/1987 | Sakakibara et al. ............ 55/137 |
| 4,711,795 A | * | 12/1987 | Takeuchi et al. ............. 427/130 |
| 4,713,724 A | * | 12/1987 | Voelkel ....................... 361/231 |
| 4,789,801 A | * | 12/1988 | Lee .............................. 310/308 |
| 5,087,428 A | * | 2/1992 | Fletcher et al. ......... 422/186.07 |
| 5,145,733 A | * | 9/1992 | Kadokura ..................... 428/551 |
| 5,186,802 A | * | 2/1993 | Kadokura ................. 204/181.4 |
| 5,656,063 A | * | 8/1997 | Hsu ............................... 95/58 |
| 5,837,035 A | * | 11/1998 | Braun et al. .................... 95/78 |

* cited by examiner

Primary Examiner—Jill Warden
Assistant Examiner—Monzer R. Chorbaji
(74) Attorney, Agent, or Firm—Armstrong, Westerman & Hattori LLP

(57) ABSTRACT

An air-cleaning apparatus and air-cleaning method whereby air is cleaned with an air flow containing ions and ozone generated by corona discharge. The apparatus has a wind tunnel part including a trumpet-shaped member (3) having an opening at the bottom thereof and a cylindrical member (4) connected to the opening at the bottom of the trumpet-shaped member (3). The wind tunnel part has a titanium dioxide metal evaporated onto the surface thereof. A needle electrode (1) is placed in front of the trumpet-shaped member (3) of the wind tunnel part near an axis of the trumpet-shaped member (3). An annular electrode is formed on the inner surface of the wind tunnel part. A high-voltage generating unit applies a high voltage between the needle electrode (1) and the annular electrode (2). A housing (10) accommodates the needle electrode (1), the annular electrode (2) and the wind tunnel part and has an air inlet (11) on a side thereof closer to the needle electrode. The housing (10) further has an air outlet (12) on a side thereof closer to the cylindrical member of the wind tunnel part. Corona discharge is induced by applying a high voltage between the needle and annular electrodes, thereby generating an air flow containing ions and ozone and thus cleaning air.

14 Claims, 8 Drawing Sheets

| | RATE OF REDUCTION AFTER 60 min. |
|---|---|
| PHOTO-IRRADIATION | 99% |
| DARK | 17% |

| | 0 HOUR | 3 HOURS |
|---|---|---|
| PHOTO-IRRADIATION | $5 \times 10^4$ | BELOW LIMIT OF DETECTION |
| DARK | $5 \times 10^4$ | $3 \times 10^4$ |

(PIECE/SAMPLE)

AIR-CLEANING APPARATUS AND AIR-CLEANING METHOD

BACKGROUND OF THE INVENTION

The present invention relates to an air-cleaning apparatus and air-cleaning method whereby air is cleaned with an air flow containing ions and ozone generated by corona discharge.

There has been proposed an ozonizer that generates an air flow containing ions and ozone through corona discharge induced by applying a high voltage between electrodes (see Japanese Utility Model Application Post-Examination Publication No. 8-9137). In this ozonizer, a cylindrical electrode and a needle electrode are used. The needle electrode is placed outside one opening of the cylindrical electrode at a predetermined distance therefrom so as to lie approximately in the center of the cylindrical electrode. A high voltage is applied between the two electrodes to generate ions and ozone and also induce an air flow containing ions and ozone that flows out from the other opening of the cylindrical electrode. Thus, the ozonizer induces an ozone-containing air flow and therefore makes it possible to dispense with the need for a motor fan and hence possible to save energy. Furthermore, the ozonizer collects fine dust particles with the electrodes.

However, the above-described conventional ozonizer suffers from various problems. For example, the volume of ozone-containing air generated by the conventional ozonizer is unfavorably small. Therefore, it is difficult for the ozonizer to generate an ozone-containing air flow at a sufficiently high flow rate. Moreover, a high ozone concentration is rather unfavorable for the environment, but the conventional ozonizer cannot reduce the amount of ozone generated. In addition, the conventional ozonizer cannot achieve a satisfactory deodorizing effect. Therefore, a perfume must be used to mask the odor of ozone and strong odors in a room. Furthermore, because fine dust particles are collected with the electrodes, it is necessary to clean the electrodes. When handling the ozonizer to clean the electrodes, great care must be taken because a high voltage is applied between the electrodes.

SUMMARY OF THE INVENTION

In view of the above-described circumstances, an object of the present invention is to control the generation of ozone, perform deodorization, sterile filtration and antifungal treatment, and thereby minimize problems attended with ozone.

To attain the above-described object, the present invention provides an air-cleaning apparatus adapted to clean air with an air flow containing ions and ozone generated by corona discharge. The air-cleaning apparatus has a wind tunnel part including a trumpet-shaped member having an opening at a bottom thereof and a cylindrical member connected to the opening at the bottom of the trumpet-shaped member. The wind tunnel part has a titanium dioxide metal evaporated onto the surface thereof. A needle electrode is placed in front of the trumpet-shaped member of the wind tunnel part near an axis of the trumpet-shaped member. An annular electrode is formed on the wind tunnel part. The air-cleaning apparatus further has a high-voltage generating unit that applies a high voltage between the needle electrode and the annular electrode. Corona discharge is induced by applying the high voltage between the needle electrode and the annular electrode, thereby generating an air flow containing ions and ozone that flows from the trumpet-shaped member toward the cylindrical member, and thus cleaning air.

The wind tunnel part has the annular electrode formed from the whole or part of the trumpet-shaped member. The needle electrode includes a plurality of needle electrodes placed on an axis of the wind tunnel part or near the axis. A guide wire having titanium dioxide evaporated thereonto is placed at an opening of the cylindrical member on a side thereof remote from the trumpet-shaped member. A housing accommodates the needle electrode, the annular electrode and the wind tunnel part, together with a plate having titanium dioxide or/and zinc oxide evaporated thereonto. The housing has an air inlet provided on a side thereof closer to the needle electrode. The housing further has an air outlet provided on a side thereof closer to the cylindrical member of the wind tunnel part. The housing has an inner wall surface coated with an amorphous metal of copper, nickel and phosphorus and a ceramic powder of aluminum oxide. The housing has a titanium dioxide-evaporated plate provided near the inner wall thereof. Another titanium dioxide-evaporated plate is provided near the air inlet. The housing may be a part of an air-conditioning duct.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

DESCRIPTION OF PREFERRED EMBODIMENTS

Figure 1A:
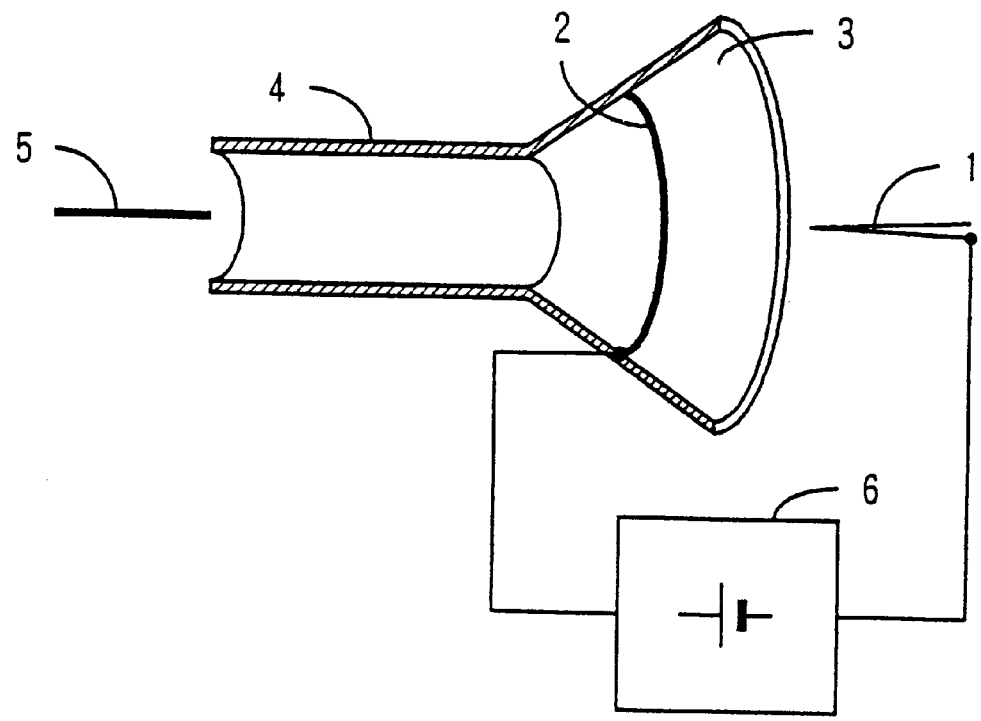
FIG. 1 is a longitudinal sectional view showing an embodiment of the air-cleaning apparatus according to the present invention.
Figure 1B:
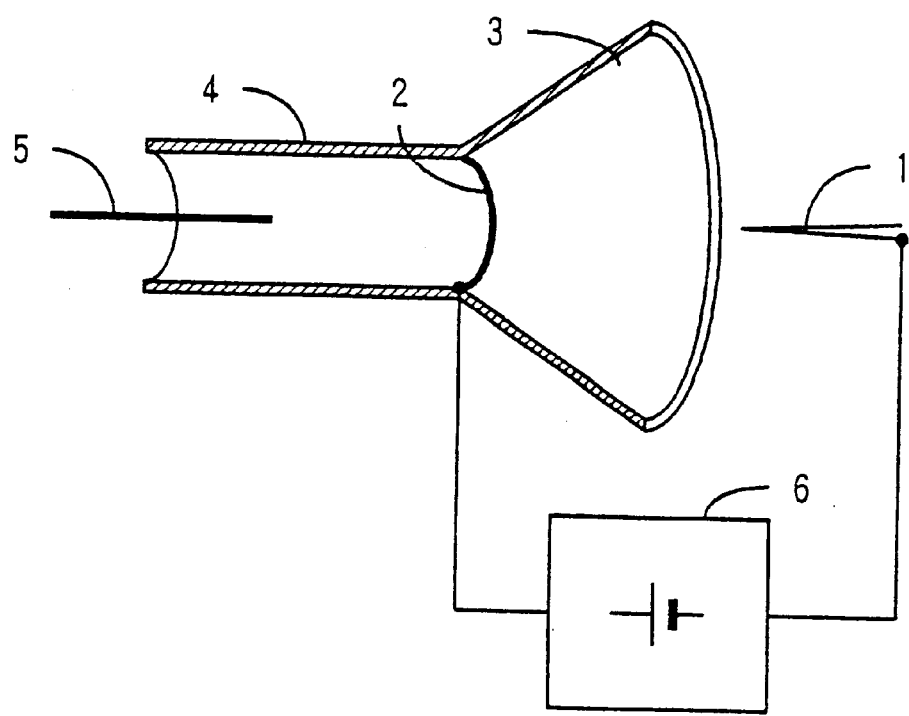

Referring to part (A) of FIG. 1, a trumpet shaped member 3 has a first opening and a second opening larger than the first opening. A cylindrical member 4 is connected to the first opening of the trumpet shaped member 3. The trumpet-shaped member 3 and the cylindrical member 4 form a wind tunnel part. The wind tunnel part has titanium dioxide and a zinc oxide metal, or a titanium dioxide metal, or a zinc oxide metal evaporated onto the outer and inner peripheral surfaces thereof. An annular electrode 2 is formed with a predetermined width on a part of the trumpet-shaped member 3. As shown in part (A) of FIG. 1, the annular electrode 2 may be formed on an intermediate part of the trumpet-shaped member 3. Alternatively, the annular electrode 2 may be formed on the bottom of the trumpet-shaped member 3, as shown in part (B) of FIG. 1, or on the distal end of the trumpet-shaped member 3. A needle electrode 1 is placed in front of the trumpet-shaped member 3 on an axis thereof so as to face opposite to the annular electrode 2. The needle electrode 1 and the annular electrode 2 also have titanium dioxide and a zinc oxide metal, or a titanium dioxide metal, or a zinc oxide metal evaporated thereonto. A high-voltage generating unit 6 generates a high voltage of 90,000 volts through a converter by using a battery, for example, as a power source. The high voltage is applied between the needle electrode 1 and the annular electrode 2 to generate an air flow containing ions and ozone. A guide wire 5 has a titanium dioxide metal evaporated thereonto. The guide wire 5 guides the ion-ozone containing air flow that is sent out from the opening at the other end of the cylindrical member 4 of the wind tunnel part.

As stated above, the trumpet-shaped member 3 is connected to the opening at one end of the cylindrical member 4 to form a wind tunnel part. This structure facilitates the generation of such a natural air flow that air is sucked in from the distal end of the trumpet-shaped member 3, and air is discharged from the opening at the other end of the cylindrical member 4. This has been proved by a wind channel test. Accordingly, when the high voltage from the high-voltage generating unit 6 is applied between the annular electrode 2, which is formed on the trumpet-shaped member 3, and the needle electrode 1, which is placed on the axis in front of the trumpet-shaped member 3 as stated above, corona discharge occurs between the needle electrode 1 and the annular electrode 2, and negative ions and ozone are generated. Consequently, a light air flow containing negative ions and ozone is induced toward the annular electrode 2 from the needle electrode 1. The air flow is intensified by the amplifying action of the wind tunnel.

Ozone has sterilizing, deodorizing and smoke-consuming effects. Sterilization is attributed to a scientific mechanism induced by the strong oxidizing action of ozone. Therefore, the speed of sterilization by ozone is much higher than in the case of sterilization by chlorine or other sterilizing methods. The sterilizing effect of ozone is several tens of times stronger than sterilization by chlorine. It is said that the bacteria sterilizing capacity of ozone is from several hundreds to several thousands of times higher than that of chlorine. Meanwhile, bad-smelling smoke is suspended in the air in the form of particles. Ozone has the function of decomposing carbon monoxide, which is a main component of cigarette smoke. Hydrogen sulfide is one of particularly bad-smelling gases. Ozone completely decomposes such a bad-smelling gas and is therefore capable of removing offensive odors. In addition, ozone has smoke-consuming and bleaching actions whereby color components of nicotine and tar contained in cigarette smoke are decomposed.

Negative ions are formed in nature by ionization of air (Lennard phenomenon) in which when small droplets of water break in the air, the droplets of water are charged positively, and the surrounding air is charged negatively. Thus, negative ions occur mainly at ravines and mountainous regions, e.g. falls and rapid streams. On the other hand, polluted air in urban areas and living spaces contains a small amount of negative ions but has a relatively high content of positive ions instead. It is well known that negative ions have a blood-purifying action, cell-activating action, vital resistance-increasing action and autonomic nerve-adjusting action and further have a sedative action, hypnotic action, anhidrotic action, appetite-increasing action, hypotensive action, refreshing action, and fatigue preventing and relieving actions.

Titanium dioxide and zinc oxide themselves are catalysts, which do not change, and therefore have the advantageous feature that the performance is maintained semipermanently. When ultraviolet rays impinge on titanium dioxide (particle diameter: from 7 to 10 nanometers), which is a catalyst, electrons and holes are generated on the surface thereof. The electrons reduce oxygen in the air to form superoxide ions, whereas the holes oxidize moisture to form hydroxyl radicals. Superoxide ions and hydroxyl radicals are generally called active oxygen, which has a strong oxidative destruction action. With this power, active oxygen kills bacteria attached to the surface of the photocatalyst and removes odors. In other words, active oxygen serves as a strong oxidizing agent and decomposes odor molecules, bacteria, etc. by the oxidizing effect. Such a photocatalytic effect is exhibited when a titanium dioxide-evaporated plate 15 (shown in FIG. 2) is irradiated with ultraviolet rays in a room, and also exhibited when a titanium dioxide-evaporated plate 7 (shown in FIG. 2) is irradiated with ultraviolet rays resulting from corona discharge induced in the electrode part.

When black carbonized residues (sludge) of organic compounds, biological particles and suspended particulate substances, which are contaminants, are attached to the electrodes, the ion-ozone generation efficiency is degraded. Vapor deposition of a titanium dioxide metal on the surface of the wind tunnel part, which is formed from the trumpet-shaped member 3 and the cylindrical member 4, produces a photocatalytic effect and effectively prevents contaminants and fine dust particles in the indoor air from adhering to the wind tunnel part.

Figure 2A:
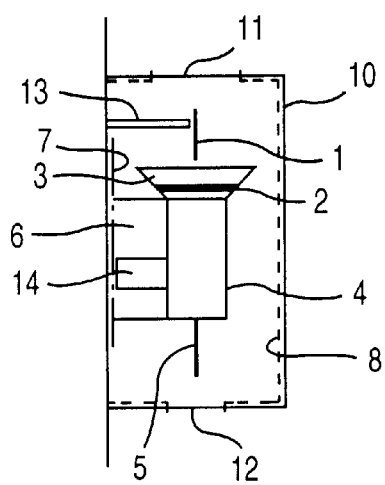
FIG. 2 is a diagram showing the embodiment of the air-cleaning apparatus according to the present invention as accommodated in a housing.
Figure 2B:
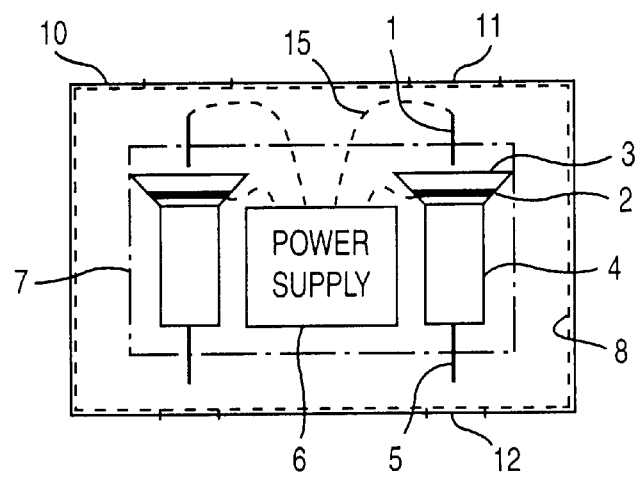
Figure 2C:
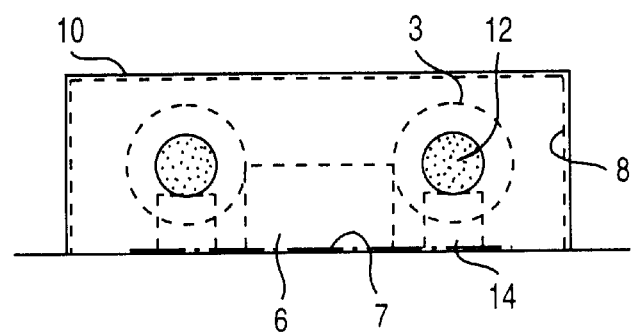

Referring to FIG. 2, a stainless steel mesh, for example, is attached to each of an air inlet 11 and an air outlet 12 to prevent large dust particles that might otherwise short-circuit the needle electrode 1 and the annular electrode 2 from entering a housing 10. The housing 10 has an amorphous metal coating surface on its inner wall. The amorphous metal coating surface is formed by coating an amorphous metal of copper Cu, nickel Ni and phosphorus P, and a ceramic powder of aluminum oxide.

In FIG. 2, part (A) is a side view showing an example of the interior layout, and part (B) is a front view showing the example of the interior layout. Part (C) of FIG. 2 is a bottom view showing the example of the interior layout. The housing 10 is a casing formed by using, for example, steel plate or a plastic or other synthetic resin material. The housing 10 is adapted to be installed on a wall surface or a ceiling surface. The housing 10 has an air inlet 11 on one side thereof and an air outlet 12 on the other side thereof opposite to the air inlet 11. The housing 10 further has an amorphous metal coating surface 8 formed on its inner wall. An ion-ozone generating unit comprises the needle electrode 1, the annular electrode 2, the trumpet-shaped member 3 and the cylindrical member 4, which have been described in connection with FIG. 1. The ion-ozone generating unit is placed in the housing 10 between the air inlet 11 and the air outlet 12 such that the needle electrode 1 is closer to the inner side of the air inlet 11. The titanium dioxide-evaporated plate 7 is placed on the bottom of the housing 10 to lie at the inner side of the ion-ozone generating unit. A retainer 13 retains the needle electrode 1 in a predetermined position. A retainer 14 retains the wind tunnel part, which comprises the trumpet-shaped member 3 and the cylindrical member 4. The retainers 13 and 14 may be arranged in an integral structure so as to retain the needle electrode 1 on the axis of the wind tunnel structure and maintain a constant distance between the needle electrode 1 and the annular electrode 2, which is provided on the trumpet-shaped member 3. In addition, the high-voltage generating unit 6 is placed in the housing 10 and connected to the needle electrode 1 and the annular electrode 2 through wiring 1S to apply a high voltage between the two electrodes 1 and 2. It should be noted that a stainless steel mesh, for example, is attached to each of the air inlet 11 and the air outlet 12 to prevent large dust particles that might otherwise short-circuit the needle electrode 1 and the annular electrode 2 from entering the housing 10. The amorphous metal coating surface 8 is formed by coating an amorphous metal of copper Cu, nickel Ni and phosphorus P and a ceramic powder of aluminum oxide. The titanium dioxide-evaporated plate 7 is has titanium dioxide and a zinc oxide metal, a titanium dioxide metal or a zinc oxide metal evaporated thereonto as in the case of the wind tunnel part.

Although in FIG. 2 two ion-ozone generating units, each comprising the needle electrode 1, the annular electrode 2, the trumpet-shaped member 3 and the cylindrical member 4, are arranged in parallel as an example of the interior layout of the housing 10, it should be noted that the number of ion-ozone generating units used may be properly increased according to a capacity required on each particular occasion. The air-cleaning apparatus may use only one ion-ozone generating unit on some occasions. In a case where the air-cleaning apparatus has a plurality of ion-ozone generating units, the number of units to be operated may be controlled according to circumstances, e.g. the condition of contamination of the indoor air, or time periods. For this purpose, a control unit that uses a timer may be provided so that a plurality of ion-ozone generating units can be started and stopped under the control of a program. Although the high-voltage generating unit 6 is disposed between the two ion-ozone generating units, the position, size and configuration of the high-voltage generating unit 6 may be properly selected according to the condition of the space in the housing 10. That is, the installation position of the high-voltage generating unit 6 may be selected from among various portions of the housing 10, e.g. the bottom, the side wall and the top. It is also possible to install the high-voltage generating unit 6 outside the housing 10 as a separate unit. The titanium dioxide-evaporated plate 7 may also be provided between the ion-ozone generating units and the front panel of the housing 10 or at a side of the ion-ozone generating unit although in the illustrated example the titanium dioxide-evaporated plate 7 is placed on the bottom of the housing 10, i.e. at the inner side of the ion-ozone generating units.

The air-cleaning action of the air-cleaning apparatus according to the present invention will be described below. When a high voltage is applied between the needle electrode 1 and the annular electrode 2 from the high-voltage generating unit 6, a light air flow containing negative ions and ozone is generated by corona discharge occurring between the two electrodes 1 and 2. In addition, ultraviolet rays are produced. The light air flow containing negative ions and ozone is amplified toward the cylindrical member 4 from the trumpet-shaped member 3 of the wind tunnel part. The ultraviolet rays cause a photocatalytic action with the titanium dioxide of the titanium dioxide-evaporated plate 7 and also causes a fusing reaction with the copper Cu, nickel Ni, phosphorus P and aluminum oxide of the amorphous metal coating surface 8, thereby changing ozone ($O_3$) into active oxygen ($O_2$) in its initial stage. The photocatalytic action of the titanium dioxide of the titanium dioxide-evaporated plate 7, together with the oxidizing action of zinc oxide, kills fungi, bacteria, methicillin (MRSA), etc., causes formaldehyde to change its property to thereby effect deodorization, and removes other organic particles. Vapor deposition of titanium dioxide on the needle electrode 1 and on the inner and outer surfaces of the wind tunnel part prevents adhesion of carbonized particles, etc. Accordingly, it is possible to dispense with the need for a cleaning operation conventionally needed to remove attached particles from the electrode part to which a high voltage is applied.

Figure 3A:
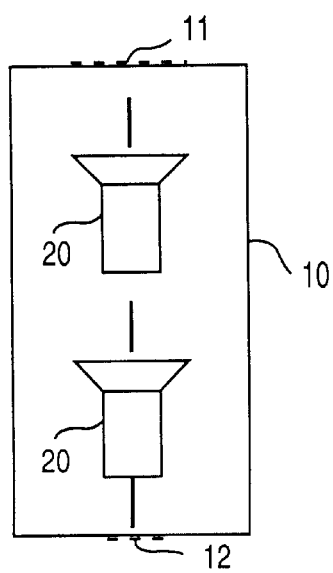
FIG. 3 is a diagram showing another embodiment of the air-cleaning apparatus according to the present invention as accommodated in a housing.
Figure 3B:
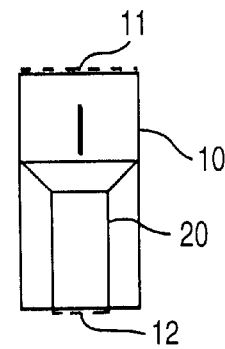
Figure 3C:
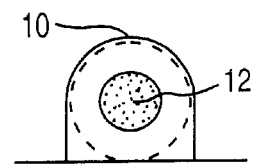

Although in the foregoing embodiment a plurality of ion-ozone generating units are arranged in parallel, as shown in part (A) of FIG. 3, ion-ozone generating units 20 may be placed in series connection with each other in the housing 10. In other words, the ion-ozone generating units 20 may be connected in a multistage structure. By doing so, the ion-ozone containing air flow induced in an up-streamside ion-ozone generating unit 20 can be further amplified in a downstream-side ion-ozone generating unit 20. If the opening at the downstream end of the cylindrical member of the ion-ozone generating unit 20 is connected directly to the air outlet 12 as shown in part (B) of FIG. 3, the size of the housing 10 can be reduced. If the housing 10 is formed in a tunnel shape in conformity to the outer diameter of the trumpet-shaped member as shown in part (C) of FIG. 3, a compact air-cleaning apparatus can be realized.

Figure 4:
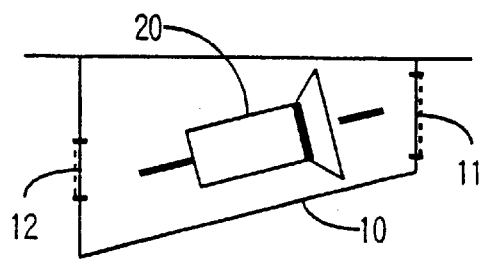
FIG. 4 is a diagram showing another embodiment of the air-cleaning apparatus according to the present invention as accommodated in a housing.

The air-cleaning apparatus according to the present invention needs no motor fan and has only a needle electrode, an annular electrode, a wind tunnel part and a high-voltage generating unit accommodated in a housing. Therefore, a compact and lightweight air-cleaning apparatus can be constructed. Accordingly, the air-cleaning apparatus can be readily installed on a wall surface or a ceiling surface, and thus it can be arranged as a wall type or a table or shelf type. In such a case, the wind tunnel part may lie horizontally, depending upon the condition in which the air-cleaning apparatus is installed or placed. If the wind tunnel part is placed horizontally, dust and residues of particulate carbon and so forth due to the electric discharge will collect on the wind tunnel part and on the inner surface of the annular electrode. To prevent such residues from collecting, the ion-ozone generating unit 20, which comprises the needle electrode 1, the annular electrode 2, the trumpet-shaped member 3, the cylindrical member 4 and the guide wire 5, may be tilted in the housing 10 with respect to the surface on which the air-cleaning apparatus is installed. An example of such an arrangement is shown in FIG. 4.

Figure 5A:
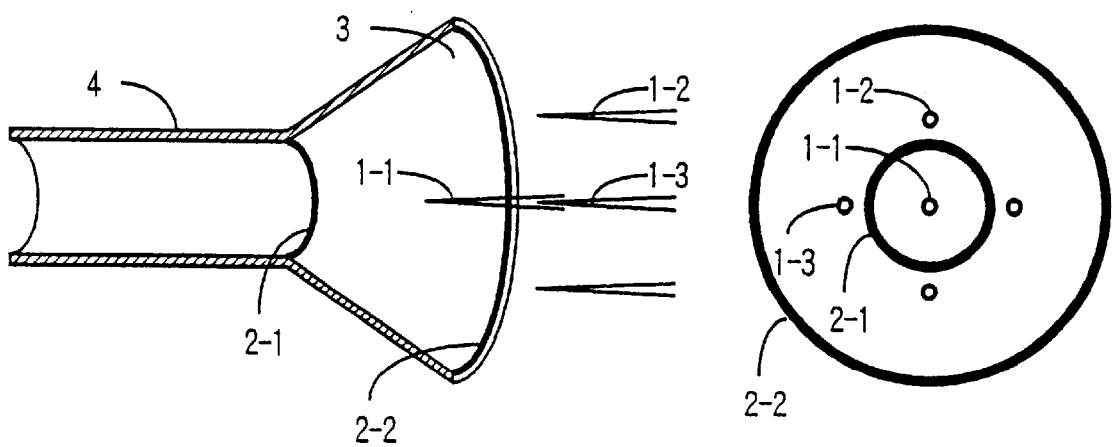
FIG. 5 is a diagram showing an ion-ozone generating unit according to another embodiment of the air-cleaning apparatus of the present invention.
Figure 5B:
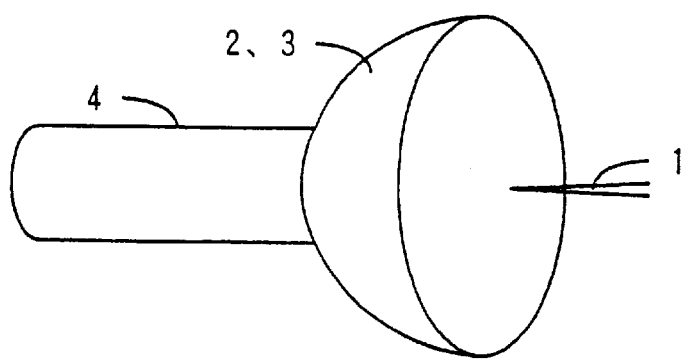

Part (A) of FIG. 5 shows an example of an arrangement in which an ion-ozone generating unit has a combination of a plurality of needle electrodes and a plurality of annular electrodes. In the arrangement shown in part (A) of FIG. 5, a needle electrode 1-1 is placed on the axis of the wind tunnel part and close to it, and a plurality of needle electrodes 1-2, 1-3, etc. are placed around the needle electrode 1-1 at respective positions more away from the wind tunnel part than the needle electrode 1-1. An annular electrode 2-1 is provided on the bottom of the trumpet-shaped member 3 so as to face opposite to the axial needle electrode 1-1, and an annular electrode 2-2 is provided on the distal end portion of the trumpet-shaped member 3 so as to face opposite to the needle electrodes 1-2, 1-3, etc., which are provided around the axis. Accordingly, a high voltage is applied between the needle electrode 1-1 and the annular electrode 2-1 and also between the needle electrodes 1-2, 1-3, etc. and the annular electrode 2-2. The number of needle electrodes 1-2, 1-3, etc. may be two or three, which may be provided to face each other vertically or horizontally. Alternatively, the number of needle electrodes 1-2, 1-3, etc. to which a high voltage is to be applied may be switched between four and two. It is also possible to provide a plurality of annular electrodes on an intermediate portion of the trumpet-shaped member 3. The axial section of the trumpet-shaped member 3 is not necessarily limited to a straight-line shape as shown in part (A) of FIG. 5, but may be curved as shown in part (B) of FIG. 5.

Figures 6A, 6B, 6C:
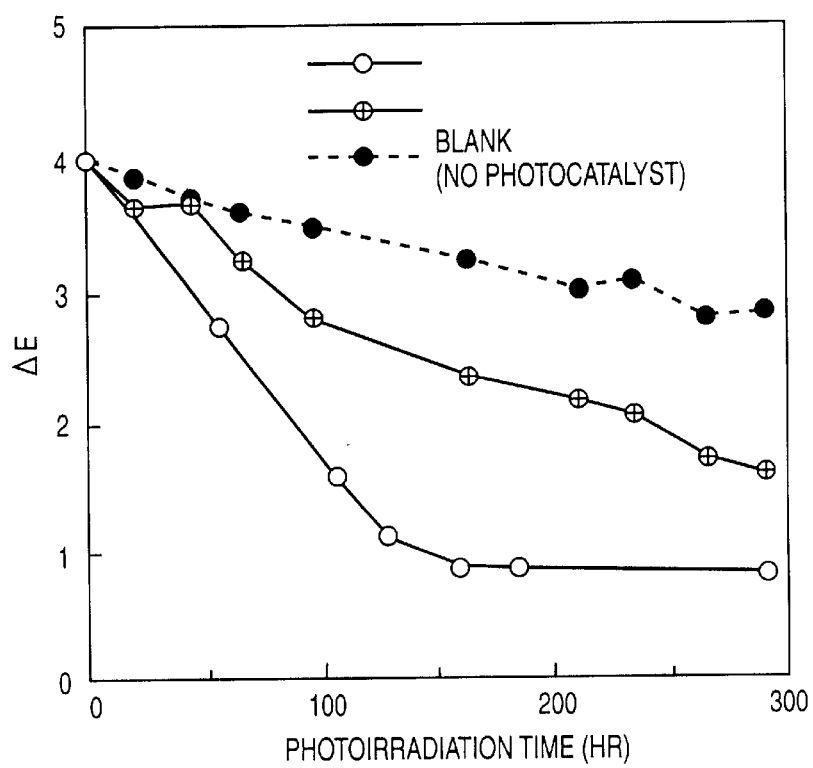
FIG. 6 is a diagram showing examples of the activity of a titanium dioxide photocatalyst.

Considering the rate of reduction of acetaldehyde after 60 minutes from the initial concentration of 96.6 ppm, as shown in part (A) of FIG. 6, it is as high as 99% when acetaldehyde is irradiated with black light (ultraviolet light quantity: 1 mW/cm$^2$) in comparison to 17% in the dark. Regarding the antibacterial effect, as shown in part (B) of FIG. 6, the number of colon bacilli ($5 \times 10^4$ /sample) measured after the irradiation with black light (ultraviolet light quantity: 100 $\mu$W/cm$^2$) for 3 hours is below the lower limit of detection in comparison to $3 \times 10^4$ in the dark. Regarding the decomposition of cigarette tar, part (C) of FIG. 6 shows the change with time of the tar deposition quantity $\Delta E$ equivalent to the amount of contamination when a space of 1 liter is filled with an amount of cigarette smoke corresponding to about one third of a cigarette through a cigarette filter. As will be clear from the figure, in the case of irradiation with black light (ultraviolet light quantity: 100 $\mu$W/cm$^2$), the tar deposition quantity $\Delta E$ reduces remarkably in comparison to a case where there is no photocatalyst (shown by the mark • and dotted line).

Figure 7:
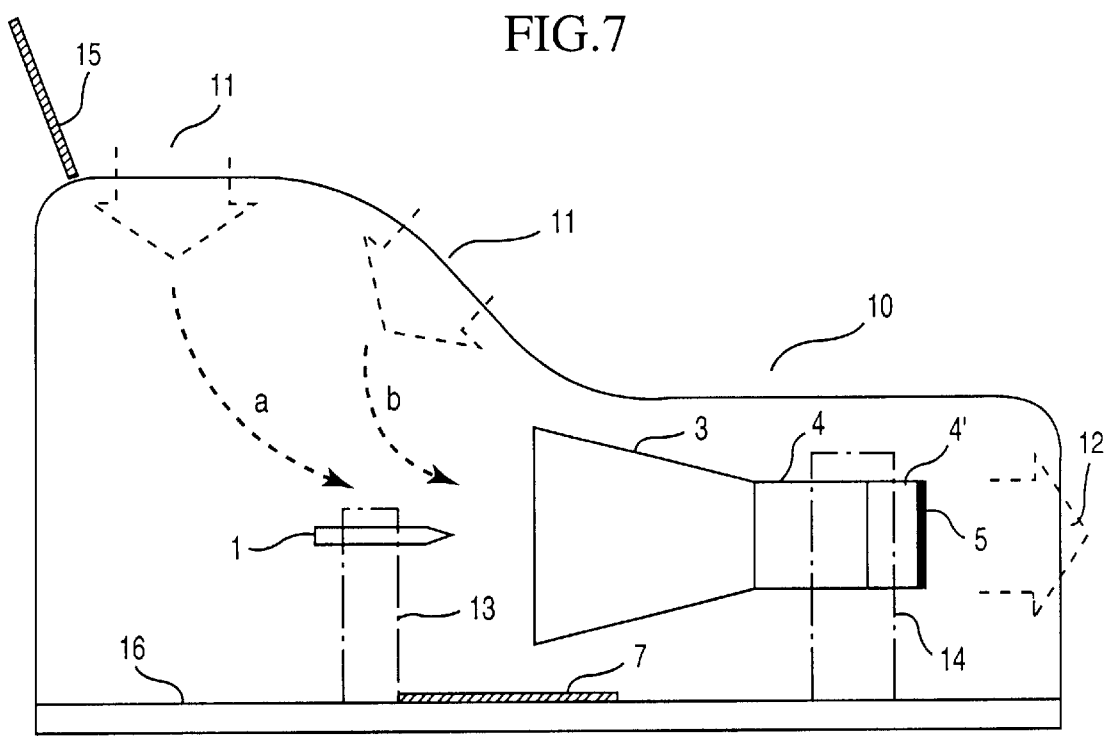
FIG. 7 is a diagram showing another embodiment of the air-cleaning apparatus according to the present invention.

Referring to FIG. 7, a housing 10 is a casing formed by using, for example, steel plate or a plastic or other synthetic resin material. The bottom surface of the housing 10 is defined as a mounting surface that is secured to a wall surface or a ceiling surface or placed on a desk or the like. The housing 10 has an air outlet 12 in a side portion at one end thereof and an air inlet 11 in a top surface at the other end thereof. The housing 10 further has an air inlet (not shown) on a side thereof opposite to the air outlet 12. A titanium dioxide-evaporated plate 15 is mounted in the vicinity of the air inlet 11. The housing 10 has a mounting base 16 therein. An air-cleaning apparatus main unit is mounted on the mounting base 16, together with a titanium dioxide-evaporated plate 7.

A support member 13 is provided on the mounting base 16 to support a needle electrode 1. A support member 14 is also provided on the mounting base 16 to support a wind tunnel part including a trumpet-shaped member 3, a cylindrical member 4, and an insulating cylinder 4' made of Teflon, for example. The needle electrode 1 is disposed to face the air inlet 11, and the insulating cylinder 4' is disposed to face the air outlet 12.

Figure 8A:
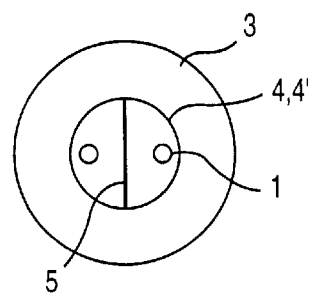
FIG. 8 is a diagram showing an electrode part of an air-cleaning apparatus main unit.
Figure 8B:
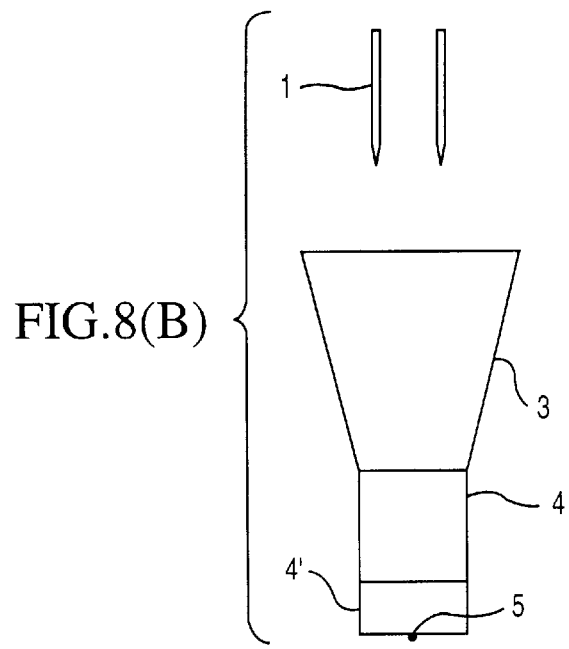

As shown in FIG. 8, the air-cleaning apparatus main unit has an electrode part comprising one or plurality of needle electrodes 1 and a trumpet-shaped member 3 that forms an annular electrode facing the one or plurality of needle electrodes 1. In addition, the cylindrical member 4 and the insulating cylinder 4' are connected in series to the opening at the bottom of the trumpet-shaped member 3. A titanium dioxide-evaporated rod 5 is provided at the opening of the insulating cylinder 4'. The trumpet-shaped member 3, the cylindrical member 4 and the insulating cylinder 4' form a wind tunnel part. The wind tunnel part has a titanium dioxide metal evaporated onto the outer and inner surfaces thereof. Similarly, each needle electrode 1 has a titanium dioxide metal evaporated onto the whole surface thereof. Part (A) of FIG. 8 shows the wind tunnel part as viewed axially from the needle electrodes 1 or from the titanium dioxide-evaporated rod 5. Part (B) of FIG. 8 shows the wind tunnel part as viewed from above.

The annular electrode may be formed from the whole trumpet-shaped member 3 as stated above. Alternatively, the annular electrode may be formed from an integral structure including the trumpet-shaped member 3 and the cylindrical member 4. The annular electrode may also be formed from a part of the trumpet-shaped member 3 or formed with a predetermined width on the inner surface of the trumpet-shaped member 3. In this case, the annular electrode may be formed on the bottom of the trumpet-shaped member 3 or on the distal end portion thereof instead of being formed on an intermediate portion of the trumpet-shaped member 3. The air-cleaning apparatus further has a high-voltage application unit (not shown) that generates a high voltage and applies it to the electrode part. A negative electrode of the high-voltage application unit is connected to the needle electrodes 1, and a positive electrode thereof is connected to the annular electrode of the trumpet-shaped member 3. The high-voltage application unit generates a high voltage of 90,000 volts through a converter by using a battery, for example, as a power source. By applying the high voltage between the needle electrodes 1 and the annular electrode, corona discharge is induced to thereby generate an ion-ozone containing air flow that flows through the wind tunnel part from the needle electrodes 1.

Figure 9:
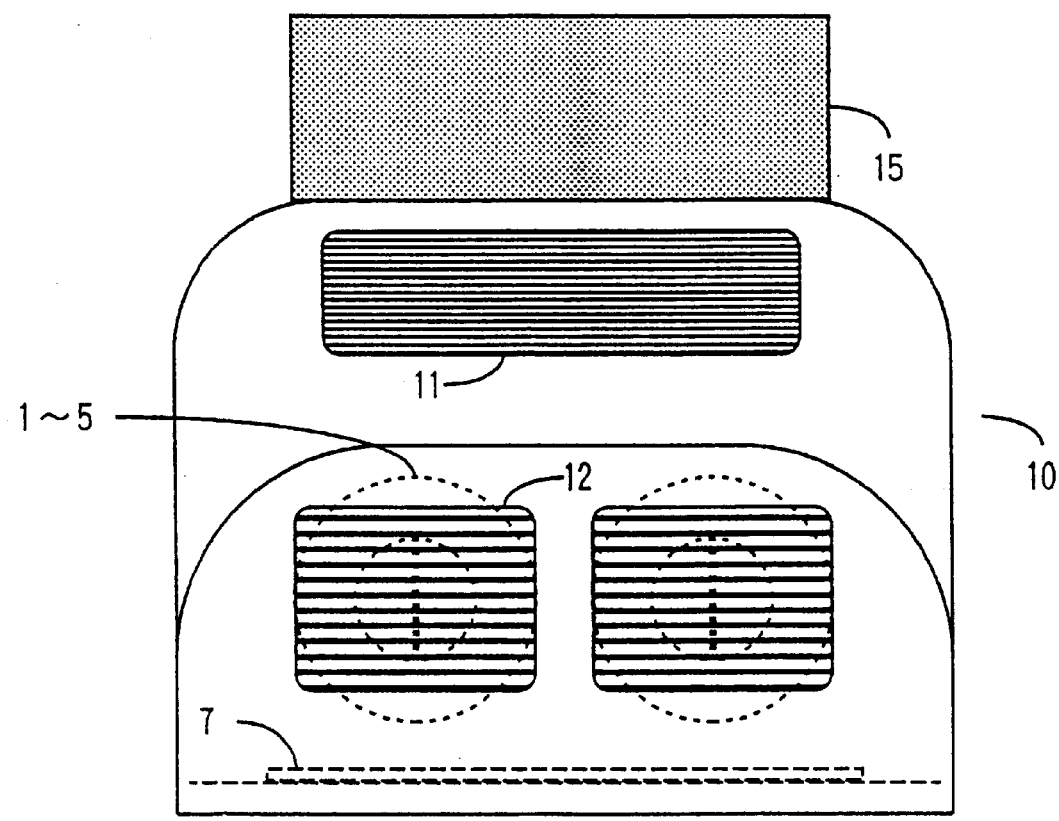
FIG. 9 is a diagram showing an external appearance of the air-cleaning apparatus as viewed from an air outlet side thereof.

In the foregoing example of the interior layout of the housing 10, as shown in FIG. 9, two air-cleaning apparatus main units are arranged in parallel in the housing 10, each unit comprising one or plurality of needle electrodes 1, a trumpet-shaped member 3 serving as an annular electrode, and a cylindrical member 4. However, it should be noted that the number of units used may be properly increased according to a capacity required on each particular occasion. The apparatus may use only one air-cleaning apparatus main unit on some occasions. In a case where the apparatus has a plurality of air-cleaning apparatus main units, the number of units to be activated may be controlled according to circumstances, e.g. the condition of contamination of the indoor air, or time periods (working hours, nighttime, morning, afternoon, holiday, etc.). For this purpose, a control unit that uses a timer or a calendar may be provided so that a plurality of air-cleaning apparatus main units can be started and stopped under the control of a program. Although the titanium dioxide-evaporated plate 7 is disposed on the bottom of the housing 10, that is, below the air-cleaning apparatus main units, it may be disposed above the air-cleaning apparatus main units or at a side thereof.

Figure 10:
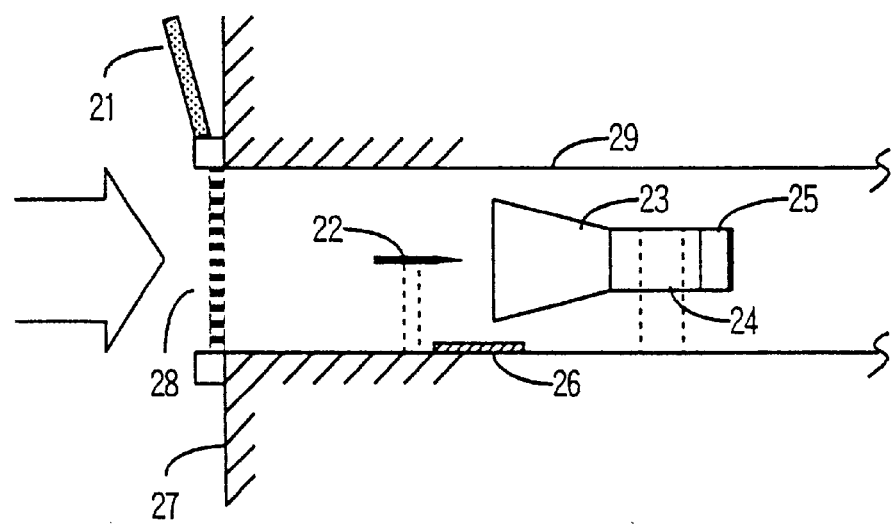
FIG. 10 is a diagram showing an embodiment in which an air-cleaning apparatus main unit according to the present invention is applied to an air-conditioning duct.

In the foregoing embodiment, the air-cleaning apparatus main units are accommodated in the housing. However, in a case where an air-cleaning apparatus main unit is accommodated in an air-conditioning duct 29 as shown in FIG. 10, no housing is needed. In this case, a needle electrode 22 and a wind tunnel part comprising a trumpet-shaped member 23, a cylindrical member 24, and a combination 25 of an insulating cylinder and a titanium dioxide-evaporated rod are installed directly in the air-conditioning duct 29. In addition, a titanium dioxide-evaporated plate 26 is installed in the vicinity of the electrode part, and a titanium dioxide-evaporated plate 21 is installed in the vicinity of an air inlet 28 for taking in air to be circulated. Furthermore, an aluminum oxide and amorphous metal coating surface is provided on a duct wall surface around the air-cleaning apparatus main unit. With this arrangement, it is possible to perform an air cleaning operation approximately equal to the operation of the air-cleaning apparatus shown in FIG. 1. It should be noted that the air-cleaning apparatus main unit may be accommodated in an air-conditioning duct of predetermined length that is used as a housing, so that the air-cleaning apparatus main unit housed in this way can be inserted into and connected to an air-conditioning duct line.

In a case where a dust collector is present in the air-conditioning duct, the air-cleaning apparatus main unit may be disposed downstream the dust collector. In a case where no external light is available and hence a sufficient photocatalytic effect cannot be obtained with only ultraviolet rays produced by corona discharge between the electrodes, the photocatalytic effect can be enhanced by providing an ultraviolet lamp in the vicinity of the air-cleaning apparatus main unit and the titanium dioxide-evaporated plate. A combination of an air-cleaning apparatus main unit, a titanium dioxide-evaporated plate and an ultraviolet lamp may be provided in an air inlet passage inside a vending machine or in a showcase for perishable foods or in a kitchen as an apparatus performing deodorization, sterile filtration, sterilization and freshness-keeping operation for canned foods, perishable foods, etc.

Results of performance tests carried out on the air-cleaning apparatus according to the present invention are as follows. First, as a deodorization test, the air-cleaning apparatus was set in a closable plastic casing and methyl mercaptan was injected into the casing through a rubber cap so that the methyl mercaptan concentration in the casing was set at 100 ppm. After 1 hour had passed, the natural attenuation was 10%, and the concentration was 90 ppm. When the methyl mercaptan concentration in the casing was set at 120 ppm and corona discharge was induced by applying a high voltage, i.e. when the air-cleaning apparatus was activated, the attenuation after 1 hour had passed was 87%, and the concentration was 14 ppm.

Next, as an antibacterial capacity test, colon bacilli and legionnaire's bacteria were dropped on a specimen, and the viable count was measured for each sample after storage for 6 hours and after storage for 24 hours. Regarding colon bacilli, the viable count of $7.6 \times 10^5$ per sample decreased to $8.3 \times 10^4$ after storage for 6 hours in an environment of 25° C. and further decreased to $5.2 \times 10^3$ after 24 hours, whereas when the air-cleaning apparatus was activated, the viable count decreased to $5.5 \times 10^4$ after 6 hours and became smaller than 10 (no bacteria were detected) after 24 hours. Regarding legionnaire's bacteria, the viable count of $6.6 \times 10^5$ decreased to $3.5 \times 10^5$ after storage for 6 hours and decreased to $3.1 \times 10^5$ after 24 hours, whereas when the air-cleaning apparatus was activated, the viable count decreased to a value smaller than 100 (no bacteria were detected) after 6 hours. For MRSA and colon bacilli (O157:H7) also, almost the same results were confirmed.

Figure 11:
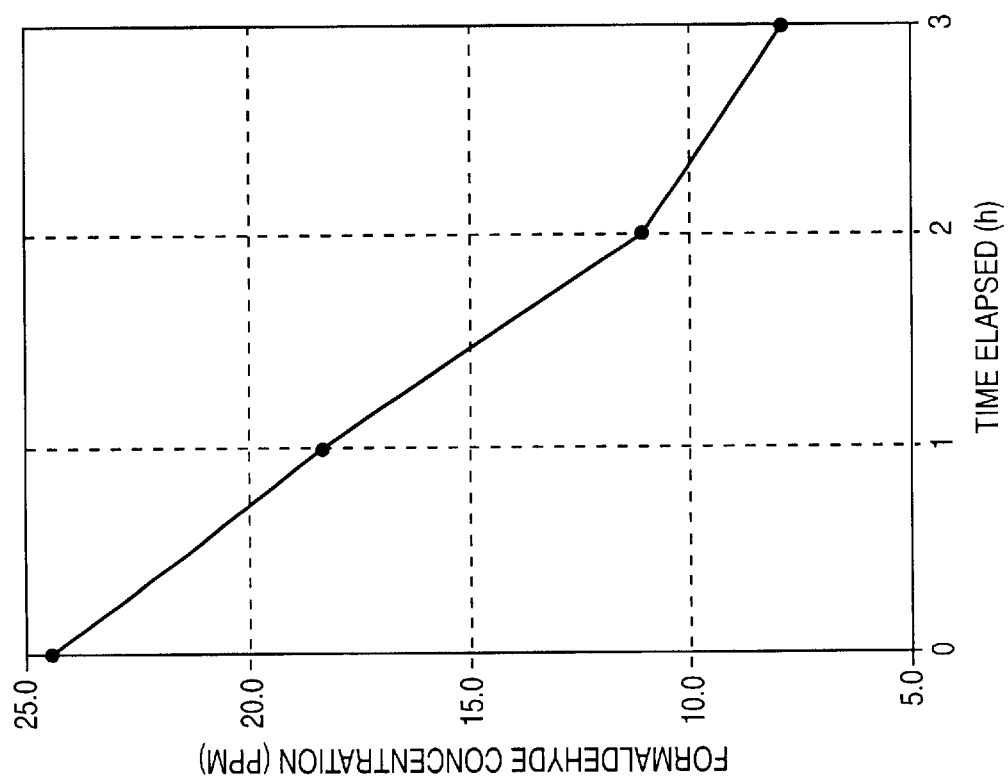
FIG. 11 is a diagram showing results of measurement concerning the removal of a malodorous substance (formaldehyde).

FIG. 11 is a diagram showing results of measurement concerning the removal of a malodorous substance (formaldehyde). The measurement was carried out as follows. A malodorous substance (formaldehyde) was put in a closed reaction vessel with a volumetric capacity of 54 liters, and changes in the formaldehyde concentration when the air-cleaning apparatus was activated and not activated were measured by gas chromatography. Measurement conditions were as follows: the temperature was 25° C.; the humidity was 70%; the initial concentration was 24.8 ppm; the detector was TCD (100 mV); the column was APS-201; INJ temperature was 150° C.; and COL temperature was 100° C. As shown in FIG. 11, the results of the measurement revealed that the rate of removal of formaldehyde was 5.63 mg/h.

Figure 12:
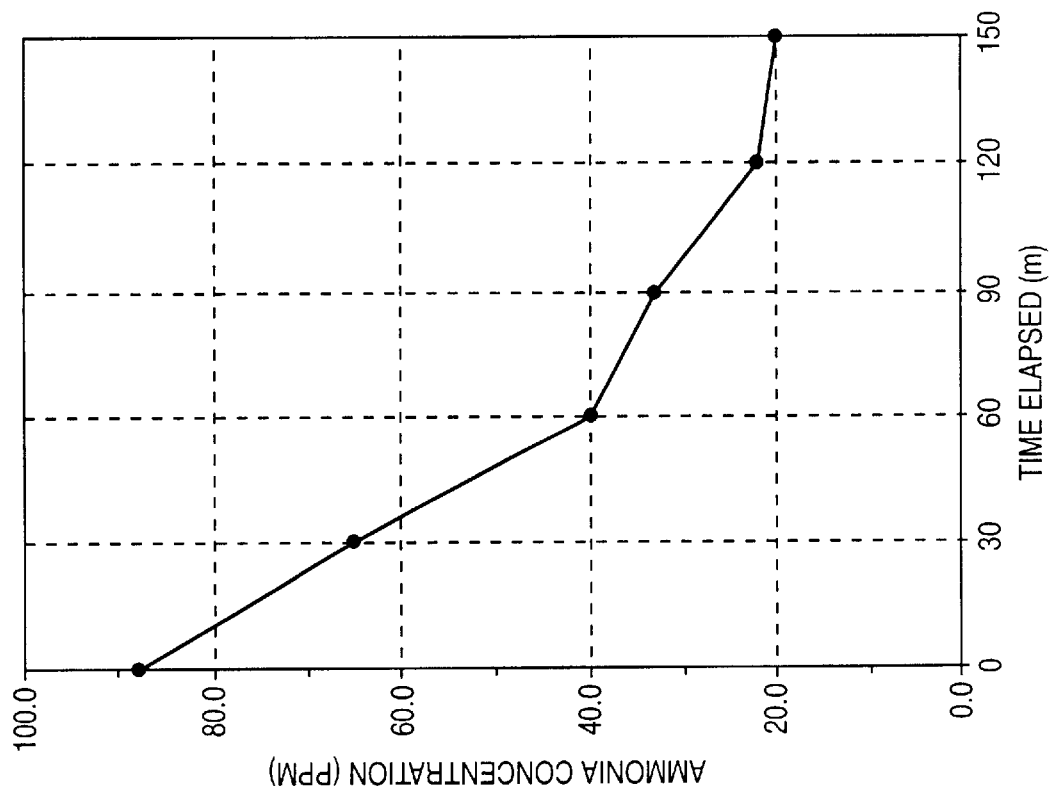
FIG. 12 is a diagram showing results of measurement concerning the removal of a malodorous substance (ammonia).

FIG. 12 is a diagram showing results of measurement concerning the removal of a malodorous substance (ammonia). Measurement conditions were as follows: the temperature was 20° C.; the humidity was 60%; the initial concentration was 87.0 ppm; and the ammonia detector was NH-275 (manufactured by Riken Keiki Co., Ltd.). As shown in FIG. 12, the results of the measurement revealed that the rate of removal of ammonia was 47.0 mg/h for an ammonia concentration of 40 ppm or higher and 13.3 mg/h for 40 ppm or lower.

Figure 14:
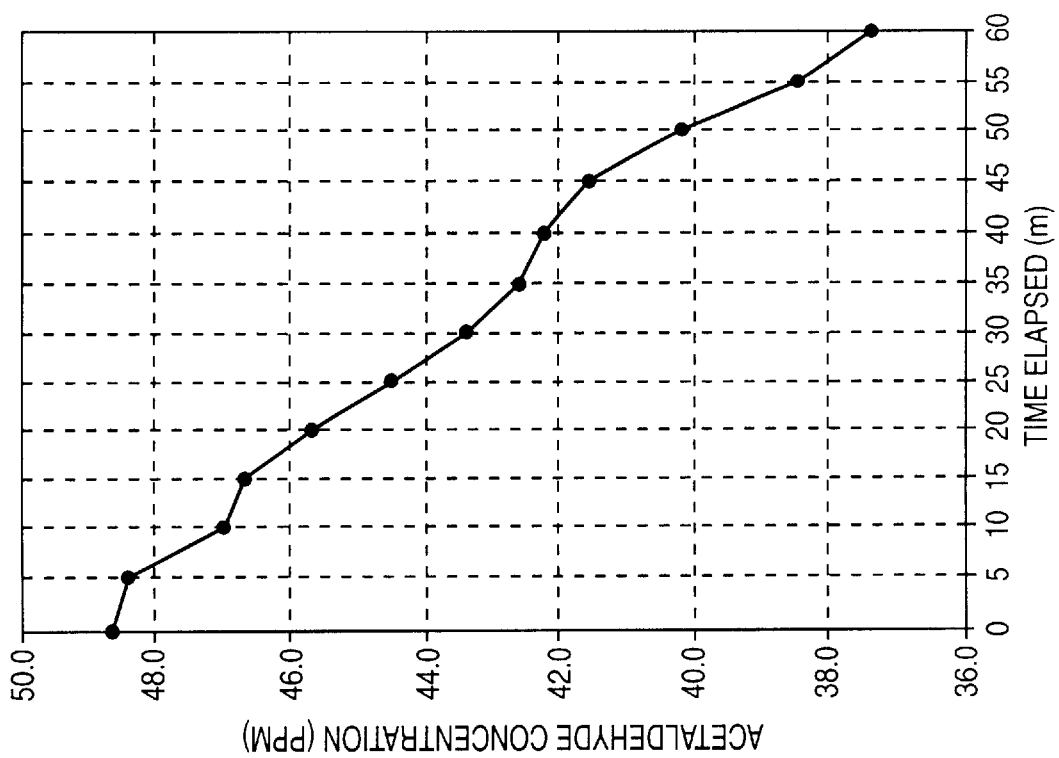
FIG. 14 is a diagram showing results of measurement concerning the removal of a malodorous substance (formaldehyde).
Figure 13:
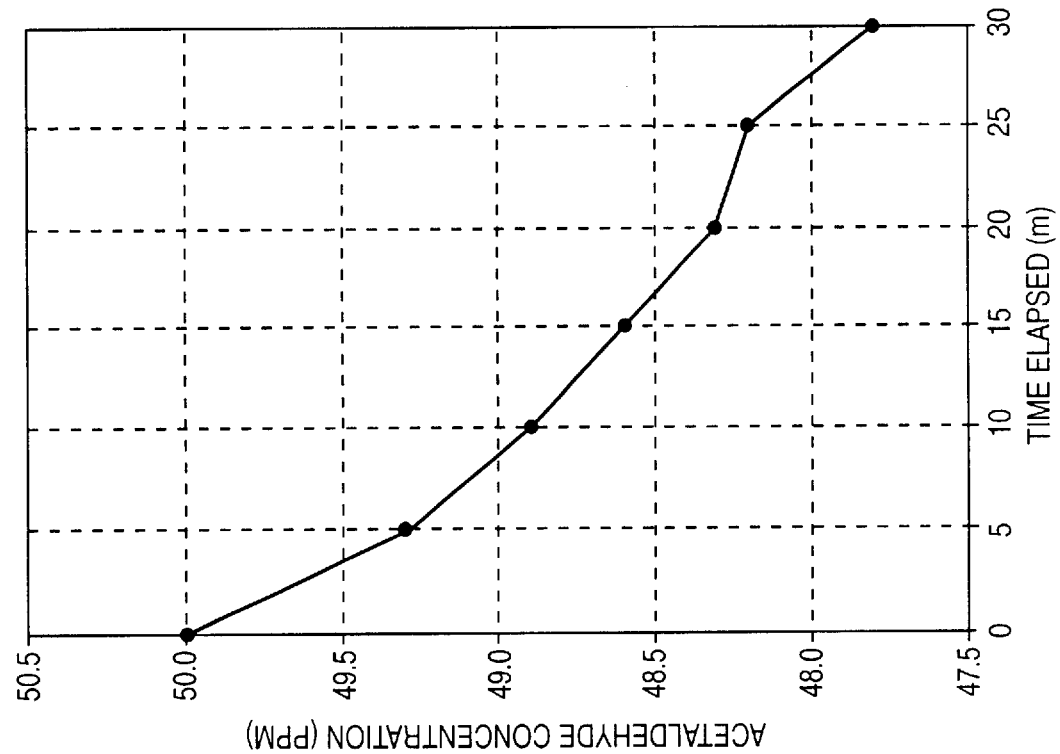
FIG. 13 is a diagram showing results of measurement concerning the removal of a malodorous substance (acetaldehyde).

FIGS. 13 and 14 are diagrams showing results of measurement concerning the removal of a malodorous substance (acetaldehyde). The measurement was carried out as follows. A malodorous substance (acetaldehyde) was put in a closed reaction vessel with a volumetric capacity of 54 liters, and changes in the acetaldehyde concentration when the air-cleaning apparatus was activated and not activated were measured by gas chromatography. Measurement conditions were as follows: the temperature was 20° C.; the humidity was 60%; the initial concentration was 50.0 ppm; the detector was TCD (100 mV); the column was APS-201; INJ temperature was 150° C.; and COL temperature was 100° C. The results of the measurement were as follows. In a case where a titanium dioxide photocatalyst alone was used, as shown in FIG. 13, the rate of removal of acetaldehyde was 436 mg/h. In a case where the air-cleaning apparatus was activated with a high voltage applied to the electrode part (i.e. when the titania window was ON), as shown in FIG. 14, the rate of removal of acetaldehyde was 11.1 mg/h.

Regarding the concentration of ozone generated by the air-cleaning apparatus according to the present invention, when the apparatus was supplied with air at a flow rate of 50 ml/s at a temperature of 20° C. and a humidity of 60%, the ozone concentration as measured by iodimetry was 0.00445 ppm per electrode. Thus, it was possible to reduce the ozone concentration to a considerable extent in comparison to a case where only electrodes having no photocatalytic action of titanium dioxide and no oxidizing action of zinc oxide were used. In a smoke-consumption experiment, 3 cigarettes were ignited in a closed reaction vessel with a volumetric capacity of 155 liters, and with the state at the time of extinguishing the cigarettes defined as an initial state, smoke consumption was observed with light energy from four 30-watt fluorescent tubes at a temperature of 21° C. and a humidity of 72%. When the air-cleaning apparatus according to the present invention was activated, a remarkable smoke-consuming effect was confirmed by visual observation.

It should be noted that the present invention is not necessarily limited to the foregoing embodiments but can be modified in a variety of ways. For example, the foregoing embodiments use the photocatalytic action of a titanium dioxide metal evaporated onto the constituent elements concerned. However, a combination of titanium dioxide and a zinc oxide metal, or a zinc oxide metal may also be evaporated onto them in place of the titanium dioxide metal. In addition, although in the above-described embodiment a plurality of air-cleaning apparatus main units are arranged in parallel, they may be connected in series, i.e. in a multistage structure. By doing so, the ion-ozone containing air flow can be further amplified. Furthermore, although each air-cleaning apparatus main unit comprises a combination of a plurality of needle electrodes and a plurality of annular electrodes, the arrangement may be such that a single needle electrode is disposed on the axis of the wind tunnel part and closer to it, and a plurality of needle electrodes are placed around the axial needle electrode at respective positions more away from the wind tunnel part than the axial needle electrode. The number of surrounding needle electrodes may be two or three, which may be provided to face each other vertically or horizontally. It is also possible to provide a plurality of axial and surrounding needle electrodes and apply a high voltage to selected needle electrodes.

As will be clear from the foregoing description, according to the present invention, a needle electrode is placed in front of a wind tunnel part formed by connecting together a trumpet-shaped member, which serves as an annular electrode, and a cylindrical member, and a high voltage is applied between the needle electrode and the annular electrode to induce corona discharge, thereby generating negative ions and ozone. Accordingly, a light air flow containing ions and ozone can be generated noiselessly without using a motor fan. Moreover, it is possible to effect sterilization, sterile filtration, deodorization and smoke consumption with high efficiency by the photocatalytic effect of a titanium dioxide-evaporated plate placed in the vicinity of an air inlet and also the photocatalytic effect of a titanium dioxide-evaporated plate placed in the vicinity of the electrode part and further the effect of an amorphous metal and negative ions by making use of light produced by the corona discharge.

Furthermore, it is possible to adjust and control the generation of an air flow containing ions and ozone by providing a plurality of needle electrodes and a plurality of annular electrodes and changing the number of electrodes used, i.e. selecting electrodes to which a voltage is to be applied, or by selecting the position of an annular electrode formed on the trumpet-shaped member. Furthermore, the housing has an inner wall surface coated with an amorphous metal of copper, nickel and phosphorus and a ceramic powder of aluminum oxide. In addition, a titanium dioxide-evaporated plate is placed in the housing near the inner wall thereof, and a titanium dioxide-evaporated rod is placed in the housing at a side thereof closer to the cylindrical member-of the wind tunnel part. Therefore, the photocatalytic action of titanium dioxide and zinc oxide enhances the deodorization, sterilization, sterile filtration and antifungal effects and causes generated ozone to change into active oxygen in its initial stage, thereby minimizing problems attended with ozone.

Furthermore, vapor deposition of titanium dioxide on the surface of the electrode part makes it possible to prevent adhesion of organic particles, suspended particulate substances, fungi, microbes, bacteria, and black carbonized particles, which would otherwise adhere to the inside of the electrode part. Accordingly, it is possible to dispense with the need for cleaning to remove substances which would otherwise adhere to the electrode part to which a high voltage is applied, and hence possible to realize a maintenance-free air-cleaning apparatus. Moreover, because a motor fan is not needed, a compact and lightweight air-cleaning apparatus can be constructed. Accordingly, the air-cleaning apparatus can be readily installed on a wall surface or a ceiling surface, and it can be arranged as a wall type or a table or shelf type.

In the air-cleaning apparatus according to the present invention, electric discharge electrodes and an evaporated film of titanium dioxide or the like are combined to thereby induce corona discharge and generate negative ions and ozone and also amplify a light air flow containing ions and ozone and realize deodorization, sterilization, sterile filtration, antifungal treatment, etc. by ultraviolet rays resulting from the corona discharge and a photocatalyst, e.g. titanium dioxide. Therefore, the air-cleaning apparatus can be effectively used during dark nighttime when lamp light or external light is unavailable, and it can be used even in a space where there is no lamp light nor external light. Accordingly, the air-cleaning apparatus can be utilized for deodorization, sterilization, sterile filtration, antibacterial treatment, antifungal treatment, product quality maintenance, etc. in a broad range of environments, i.e. ordinary residential rooms, offices, hospitals, factories, facilities, clean rooms, kitchens, air-conditioning ducts, show cases, vending machines, vehicles, etc.

I claim:

1. An air-cleaning apparatus adapted to clean air with an air flow containing ions and ozone generated by corona discharge, said air-cleaning apparatus comprising:

a wind tunnel part including a trumpet-shaped member having a first opening and a second opening larger than the first opening and a cylindrical member connected to the first opening, said wind tunnel part having a titanium dioxide metal evaporated onto a surface thereon;

a needle electrode placed in front of the second opening of the trumpet-shaped member of said wind tunnel part near an axis of said trumpet-shaped member;

an annular electrode formed on said wind tunnel part; and a high-voltage generating unit that applies a high voltage between said needle electrode and said annular electrode;

wherein corona discharge is induced by applying the high voltage between said needle electrode and said annular electrode, thereby generating an air flow containing ions and ozone that flows from said trumpet-shaped member toward said cylindrical member, and thus cleaning air.

2. An air-cleaning apparatus according to claim 1, wherein said wind tunnel part has said annular electrode formed from a whole or part of said trumpet-shaped member.

3. An air-cleaning apparatus according to claim 1, wherein said needle electrode includes a plurality of needle electrodes placed on an axis of said wind tunnel part and near said axis.

4. An air-cleaning apparatus according to claim 1, wherein a guide wire having titanium dioxide evaporated thereonto is placed at an opening of said cylindrical member on a side thereof remote from said trumpet-shaped member.

5. An air-cleaning apparatus according to claim 1, wherein said needle electrode, annular electrode and wind tunnel part are accommodated in a housing, said housing having an air inlet provided on a side thereof closer to said needle electrode, said housing further having an air outlet provided on a side thereof closer to the cylindrical member of said wind tunnel part.

6. An air-cleaning apparatus according to claim 5, wherein said housing has an inner wall surface coated with an amorphous metal of copper, nickel and phosphorus and a ceramic powder of aluminum oxide.

7. An air-cleaning apparatus according to claim 5, wherein said housing has a titanium dioxide-evaporated plate provided near an inner wall thereof.

8. An air-cleaning apparatus comprising:

a wind tunnel part including a trumpet-shaped member having a first opening and a second opening larger than the first opening and a cylindrical member connected to the first opening, said wind tunnel part having titanium dioxide or/and zinc oxide evaporated onto a surface thereof;

a needle electrode placed in front of the second opening of the trumpet-shaped member of said wind tunnel part near an axis of said trumpet-shaped member;

an annular electrode formed on said wind tunnel part; and a plate having titanium dioxide or/and zinc oxide evaporated thereonto, said plate being placed adjacent to at least said needle electrode and said annular electrode;

wherein corona discharge is induced by applying a high voltage between said needle electrode and said annular electrode from a high-voltage application unit, thereby cleaning air.

9. An air-cleaning apparatus according to claim 8, wherein said wind tunnel part has said annular electrode formed from a whole or part of said trumpet-shaped member, said needle electrode including a plurality of needle electrodes placed on an axis of said wind tunnel part or near said axis.

10. An air-cleaning apparatus according to claim 8, wherein a rod having titanium dioxide or/and zinc oxide evaporated thereonto is placed at an opening of said cylindrical member on a side thereof remote from said trumpet-shaped member with an insulating cylinder interposed therebetween.

11. An air-cleaning apparatus according to claim 8, wherein said needle electrode, annular electrode, wind tunnel part, plate having titanium dioxide or/and zinc oxide evaporated thereonto are accommodated in a housing, said housing having an air inlet on a side thereof closer to said needle electrode, said housing further having an air outlet on a side thereof closer to the cylindrical member of said wind tunnel part, and a plate having titanium dioxide or/and zinc oxide evaporated thereonto is provided near said air inlet.

12. An air-cleaning apparatus according to claim 11, wherein said housing is a part of an air-conditioning duct.

13. An air-cleaning apparatus according to claim 11, wherein said housing has an inner wall surface coated with an amorphous metal of copper, nickel and phosphorus and a ceramic powder of aluminum oxide.

14. An air-cleaning method comprising the steps of:

preparing a wind tunnel part including a trumpet-shaped member having an opening at a bottom thereof and a cylindrical member connected to the opening at the bottom of said trumpet-shaped member, a needle electrode placed in front of the trumpet-shaped member of said wind tunnel part near an axis of said trumpet-shaped member, an annular electrode formed on said wind tunnel part, and a panel having titanium dioxide or/and zinc oxide evaporated thereonto; and applying a high voltage between said needle electrode and said annular electrode from a high-voltage application unit to induce corona discharge, thereby generating a light air flow containing negative ions and ozone and cleaning air by utilizing actions of said ions and ozone and also a photocatalytic action of said titanium dioxide or/and zinc oxide.

* * * * *